United States Patent [19]
Osbon et al.

[11] Patent Number: 5,421,808
[45] Date of Patent: Jun. 6, 1995

[54] BATTERY-OPERATED MALE ORGAN CONDITIONING APPLIANCE

[75] Inventors: James B. Osbon, Richmond, Va.; Andrew Sealfon, Middleton, N.Y.; John M. Mitchell, Martinez, Ga.

[73] Assignee: Osbon Medical Systems, Ltd., Augusta, Ga.

[21] Appl. No.: 100,635

[22] Filed: Jul. 30, 1993

[51] Int. Cl.$^6$ ............................................. A61F 5/00
[52] U.S. Cl. ............................................... 600/38
[58] Field of Search ................................. 600/38–41; 128/897–899

[56] References Cited

U.S. PATENT DOCUMENTS

| | | |
|---|---|---|
| D. 299,537 | 1/1989 | Morifuji . |
| D. 307,478 | 4/1990 | Morifuji . |
| D. 317,504 | 6/1991 | Osbon . |
| D. 317,505 | 6/1991 | Osbon . |
| D. 330,081 | 10/1992 | Walsh . |
| D. 343,454 | 1/1994 | Osbon . |
| D. 343,455 | 1/1994 | Osbon . |
| D. 345,420 | 3/1994 | Stewart, Sr. . |
| D. 346,219 | 4/1994 | Färdigh . |
| 897,289 | 9/1908 | Howell . |
| 1,117,618 | 11/1914 | Ach . |
| 1,225,341 | 5/1917 | Lederer . |
| 1,963,576 | 6/1934 | Boerlage . |
| 2,011,831 | 8/1935 | Sinanide . |
| 2,533,924 | 12/1950 | Foley . |
| 2,874,698 | 2/1959 | Sell . |
| 3,421,504 | 1/1969 | Gibbons . |
| 3,631,853 | 1/1972 | Burdette, Jr. . |
| 3,744,486 | 7/1973 | Wilson . |
| 3,820,533 | 6/1974 | Jones . |
| 3,910,262 | 10/1975 | Stoughton . |
| 4,175,554 | 11/1979 | Gerow . |
| 4,203,432 | 5/1980 | Koch . |
| 4,312,350 | 1/1982 | Doan . |
| 4,323,067 | 4/1982 | Adams . |
| 4,378,008 | 3/1983 | Osbon, Sr. ......................... 600/38 |
| 4,397,639 | 8/1983 | Eschweiler et al. . |
| 4,407,275 | 10/1983 | Schroeder . |

(List continued on next page.)

FOREIGN PATENT DOCUMENTS

| | | |
|---|---|---|
| 148586A1 | 7/1985 | European Pat. Off. . |
| 2658322 | 6/1978 | Germany . |
| 2129688 | 5/1984 | United Kingdom . |
| 2155792 | 10/1985 | United Kingdom . |

OTHER PUBLICATIONS

RFSAU Medic; Vacuumpump Active Erection System Instruction Manual and Product Details, 12 pages, 1991.

One Page Flyer Entitled "Erecaid System Plus" by Osbon Medical Systems; 1991; and Two Pages of Disclosure Materials.

Marmar, et al.; "Penile Plethysmography on Impotent Men Using Vacuum Constrictor Devices"; pp. 198–203; Sep. 1988; vol. XXXII; No. 3; Urology Journal.

Corporation Bellofram; Diaphragm Design Manual; 1980; pp. 1–7; 13; 15; 18–30.

*Primary Examiner*—Lee S. Cohen
*Assistant Examiner*—J. P. Lacyk

[57] ABSTRACT

A self-contained, battery-operated, external vacuum device includes an electric motor with an eccentric output shaft coupled with a reciprocating diaphragm pump in a common housing with the electric motor and batteries. A housing vacuum port is removably mounted inline on a reversible coupler, which in turn is received in an open end of a vacuum chamber for receiving a user's flaccid penis for vacuum engorgement therapy. The reversible coupler includes a pair of concentric annular extensions for establishing a vacuum seal with the housing vacuum port. A reverse side of the coupler includes an extended coupling nipple for alternate vacuum seal attachment with tubing connected to a manual pump. The vacuum chamber is tapered towards the penis introducing end to facilitate the full engorgement of the glans penis. A relative vacuum indicator on the housing permits the user to monitor the degree of negative pressure applied to the penis, which may then be adjusted with a flow control knob mounted on the housing. The electric motor is a relatively high torque low energy consumption motor to prevent pump stall.

38 Claims, 6 Drawing Sheets

U.S. PATENT DOCUMENTS

| | | |
|---|---|---|
| 4,641,638 | 2/1987 | Perry . |
| 4,673,388 | 6/1987 | Schlensog et al. . |
| 4,718,411 | 1/1988 | Stewart . |
| 4,741,329 | 5/1988 | Marcune . |
| 4,753,227 | 6/1988 | Yanuck, Jr. . |
| 4,759,747 | 7/1988 | Aida et al. . |
| 4,803,950 | 2/1989 | Griffin et al. . |
| 4,856,498 | 8/1989 | Osbon ................................ 600/38 |
| 4,856,499 | 8/1989 | Kelly ................................. 600/38 |
| 4,883,464 | 11/1989 | Morifuki . |
| 4,886,494 | 12/1989 | Morifuji . |
| 5,020,522 | 6/1991 | Stewart . |
| 5,083,556 | 1/1992 | Osbon et al. . |
| 5,095,895 | 3/1992 | Walsh .................................. 600/39 |
| 5,125,890 | 6/1992 | Merrill et al. ....................... 600/39 |
| 5,195,943 | 3/1993 | Chaney ................................ 600/38 |
| 5,213,563 | 5/1993 | Cox ..................................... 600/38 |
| 5,234,402 | 8/1993 | Osbon . |
| 5,244,453 | 9/1993 | Osbon et al. ........................ 600/41 |
| 5,306,227 | 4/1994 | Osbon et al. . |

BATTERY-OPERATED MALE ORGAN CONDITIONING APPLIANCE

BACKGROUND OF THE INVENTION

The present invention relates in general to improved impotence treatment appliances and, in particular, to battery-operated devices improved for user controlled performance and convenience.

The problem of male impotence (i.e., the inability to gain an adequate penile erection for coitus) is well known and the subject of considerable medical and scientific attention. Heretofore, various nonsurgical and surgical therapies have been available for treatment of male impotence. One nonsurgical therapy generally makes use of a vacuum chamber device for producing penile engorgement and rigidity by using a vacuum to draw blood into the erectile bodies of the user's male sex organ, i.e., the penis. Typically, the user's penis is placed within a vacuum chamber or cylinder in order to induce vacuum engorgement. The engorged condition is then generally subsequently secured with an elastic cincture band or the like.

Commonly assigned U.S. Pat. Nos. 5,083,556 (Osbon et al.); 4,378,008 (Osbon, Sr.); and 4,856,498 (Osbon) disclose various examples of vacuum chambers for use in vacuum erection enhancement therapy. As shown, such chambers have a fixed vacuum nipple or port opposite to an open end thereof, into which the flaccid penis is placed for treatment. A vacuum tube is then interconnected to the vacuum nipple and to a vacuum source (i.e., source of negative pressure), such as a manual or hand pump. There are examples of elastic rings shown or discussed in such patents, for being initially applied to the outside diameter of the vacuum chamber, and then subsequently transferred to the base or root of the user's engorged penis, for capturing and maintaining vacuum induced rigidity thereof. Commonly assigned U.S. Pat. Nos. D 317,504 (Osbon) and D 317,505 (Osbon) illustrate other examples of elastic cincture bands.

One known somewhat problematic aspect of utilizing vacuum erection enhancement devices simply concerns the physical requirements (for example, dexterity) of handling the necessary apparatus or equipment. For example, because of the relatively small size of the resilient penile cincture band, the relatively high resiliency thereof, and the acts involved in its use, some degree of user strength and dexterity is involved with its placement as well as with the practice of the overall therapy. Of course, the degree of "difficulty" which may be encountered by users at various times can depend on a number of highly subjective factors and considerations.

In view of the foregoing, and with a general eye towards progression of the technology, a number of advancements, improvements, and other changes, have been disclosed over time. Examples of such, as follows, may be found in the patent literature.

Lederer (U.S. Pat. No. 1,225,341) very simply discloses a vacuum bulb attached directly to an open end chamber for receipt of a penis to be treated. Sell (U.S. Pat. No. 2,874,698) discloses a more developed pump mechanism, using a manual stroking piston pump assembly threadably attached to a vacuum chamber end. Gibbons (U.S. Pat. No. 3,421,504) and Burdette, Jr. (U.S. Pat. No. 3,631,853) respectively disclose various pump arrangements wherein a vacuum cylinder is connected via flexible tubing or the like to some form of manually operated pump assembly.

Marcune (U.S. Pat. No. 4,741,329) discloses a manual pump arrangement commonly received inside a housing associated directly with a vacuum housing for the user's penis. An activating lever is associated with the side of the housing, which housing also contains battery-operated stimulating mechanisms. Still further, Wilson (U.S. Pat. No. 3,744,486) discloses at least three separate embodiments wherein a vacuum chamber 12 is alternatively associated with a side mounted manual pump, a tubing interconnected vacuum bottle, and an electric cord electrical vacuum pump arrangement mounted at the end of the vacuum barrel. Yanuck, Jr. (U.S. Pat. No. 4,753,227) discloses a vacuum erection device wherein an electrical pump 20 is powered by a battery 62 directly associated with the device.

While at least in a broad sense such exemplary patents illustrate that vacuum engorgement technology has progressed from strictly manual pump arrangements to providing electrically powered devices, use of such power assisted devices is not yet widespread due to a variety of functional and practical drawbacks. For example, battery-powered devices, in general, tend to indicate lower powered devices, which could result in pump stalling during vacuum operations. Obviously, such occurrence totally defeats the purpose of the apparatus. In addition, given the sensitive nature of the medical treatment involved, any failure of the device may be considered by the user as operator error, or may for some other reason result in a frustrating experience, which is highly undesirable for such users. As with many other types of treatments, frustration levels can lead to curtailment of the therapy by the user.

In addition to the prospect of motor stall, numerous other aspects of handling or use can result in a failed product and a failed therapy. For example, the convenience of handling and using the device is itself a direct factor in success of the therapy. Also, some impotence patients suffer from various nerve damage, either through disease or age, and may not be directly sensitive to the degree of negative pressure applied to the user's penis. For such reason, the use of power assisted impotence treatment devices can create added user responsibilities for monitoring and care when using treatment products. Ideally, the apparatus itself would facilitate the monitoring and adjusting of negative pressure, even in the event of physical limitations of the user in directly sensing such pressures.

The disclosures of the above-listed patents are fully incorporated herein by reference.

SUMMARY OF THE INVENTION

The present invention recognizes and addresses various of the foregoing problems, and others, concerning impotence treatment operations. Thus, broadly speaking, a principal object of this invention is improved impotence treatment operations. More particularly, a main concern is improved impotence treatment operations involving power assisted equipment.

It is another more particular object of the present invention to provide improved apparatus for power assisted impotence treatments, such as making use of self-contained, battery-operated electric pump devices.

It is yet another particular object of the present invention to provide improved power assisted apparatus which may alternatively still be useable with manual pump mechanisms.

Still further it is another general object to provide a multi-component system which may be reconfigured specifically for use with a power assisted vacuum pump or a manually actuated pump.

It is another general object of the subject invention to provide such improved impotence treatment devices which also give consideration to the user's convenience, as well as the user's ability to handle the device. At the same time, it is desired to facilitate a user's opportunity to visually monitor and manually control the amount of negative pressure being produced with the power assisted apparatus.

By reducing motor stall, and by other improvements, it is a further present object to improve the performance and reliability of a power assisted device, so as to greatly enhance prospects of successful completion of power assisted therapy.

It is another present general object to provide a system having separable components which each contribute to various functional advantages. For example, it is desired to provide an improved vacuum chamber arrangement, which facilitates the ease of cleaning thereof, as well as the vacuum operations thereof during enlargement of the user's penis. It is further desired to provide a coupler arrangement which facilitates the alternative usage of both power assisted and manually actuated equipment, while at the same time providing effective vacuum seals which are readily and reliably established.

It is a further general object of the present invention to provide a system which may be operated in a hand-held mode as a fully self-contained batter-operated device which is highly adapted to patient usage for maximum opportunity for effectiveness of the impotence treatment vacuum therapy.

Additional objects and advantages of the invention are set forth in, or will be apparent to those of ordinary skill in the art from, the detailed description which follows. Also, it should be further appreciated that modifications and variations to the specifically illustrated and discussed features or materials hereof may be practiced in various embodiments and uses of this invention without departing from the spirit and scope thereof, by virtue of present reference thereto. Such variations may include, but are not limited to, substitution of equivalent means and features or materials for those shown or discussed, and the functional or positional reversal of various parts, features, or the like.

Still further, it is to be understood that different embodiments, as well as different presently preferred embodiments, of this invention may include various combinations or configurations of presently disclosed features or elements, or their equivalents (including combinations of features or configurations thereof not expressly shown in the Figures or stated in the Detailed Description). One exemplary such embodiment of the present invention relates to a self-contained, battery-operated male organ conditioning appliance. Such appliance comprises in combination an elongated vacuum chamber, reversible coupling and vacuum seal means, and battery-operated vacuum motor means.

Such vacuum chamber preferably has a first open end for introduction of a user's flaccid penis into such chamber, and a second open end for application of negative pressure to the chamber adequate so as to produce an erection in the user's flaccid penis. The chamber forms a reducing taper from its second open end towards its first open end. The reversible coupling and vacuum seal means preferably may be removably receivable in the vacuum chamber second open end so as to seal same against air flow except through a vacuum port defined by the member. Such member has a first vacuum port connection element for vacuum seal attachment of a vacuum tube to the vacuum port. A second vacuum port connection element is provided on a reverse side thereof for alternate vacuum seal attachment of a battery-operated vacuum motor means to the vacuum port.

Such exemplary battery-operated vacuum motor means may be provided as a source of negative pressure at an intake port thereof. The vacuum motor means further may include a collar mounting means about such intake port for selectively establishing a vacuum seal attachment between such intake port and the second vacuum port connection element whenever the reversible coupling and vacuum seal means is received in the vacuum chamber second open end such that the second vacuum port connection element is outwardly exposed. With such exemplary arrangement, negative pressure provided at the vacuum motor means intake port is transmitted via the vacuum port to the interior of the vacuum chamber. In such chamber, the negative pressure beneficially produces vacuum engorgement of a user's flaccid penis introduced thereto.

Another present exemplary embodiment concerns an inline power assisted vacuum therapy impotence treatment apparatus with separable components to provide for alternate use thereof with a manually operated pump vacuum source. Such arrangement preferably may include a vacuum chamber with opposing open ends, a generally round reversible coupler, and inline vacuum pump means.

Such exemplary vacuum chamber may have one end thereof for introduction of a user's flaccid penis and the other end thereof established for introduction of negative pressure to such chamber. The reversible coupler preferably has a generally central bore therethrough and different first and second axial sides, for selected sealing of the chamber other end with a selected one of such axial sides outwardly exposed. The first axial side may have an extending nipple for connecting an external vacuum tube in vacuum seal relationship with such central bore. The second axial side may have plural telescoped sealing elements for connecting an inline power assisted pump in vacuum seal relationship with the central bore.

Such inline vacuum pump means preferably includes a battery-operated electric motor and airflow pump arrangement with a vacuum connection port, for inline removable attachment to the reversible coupler second axial side. With such arrangement, negative pressure is provided to the vacuum chamber when the pump means is coupled thereto with the reversible coupler and via the vacuum connection port and the reversible coupler central bore, which results in therapeutic engorgement of a user's flaccid penis received in such chamber.

Yet another construction comprising a present exemplary embodiment relates to a multiple component impotence treatment system, such as comprising a tapered enclosable vacuum chamber, an elastic cincture band, a sealing coupling element, and an inline vacuum motor housing. Such housing may include a self-contained battery-operated electric motor, and a vacuum pump operable by such motor so as to provide negative pressure via the sealing coupling element to the vacuum chamber. After such negative pressure is therapeutically administered to a user's flaccid penis so as to produce vacuum engorgement thereof suitable for intercourse, such engorgement is subsequently captured by moving the elastic cincture band on to the base of the user's conditioned penis, so that the penis may be withdrawn from the vacuum chamber without loss of a penile engorgement.

A still further present exemplary embodiment relates to a self-contained hand held battery-operated vacuum motor apparatus for removable inline mounting onto the vacuum connection end of a penile receiving vacuum chamber for the therapeutic treatment of impotence. Such an exemplary apparatus preferably includes respective upper and lower mutually closable housing members, an intake coupling port, a battery-operated electric motor, a battery compartment, motor power switch means, reciprocating diaphragm pump means, user actuatable vacuum release means, relative vacuum indicator means, and user actuable flow control means. With the foregoing exemplary arrangement, a user may visually monitor and manually control the amount of negative pressure produced with the indicated power assisted device, even if the user is incapable of directly perceiving negative pressure on his penis with his physical senses. Hence, the indicated arrangement provides for improved comfort and safety during user controlled vacuum engorgement therapy treatments.

Also, some present exemplary embodiments relate to specific embodiments of a reversible coupler for use with a vacuum therapy impotence treatment system, such as including a penile vacuum chamber, an elastic cincture band, a manual pump with interconnecting vacuum tubing, and an alternate battery-operated pump with an inline negative pressure port.

Those of ordinary skill in the art will better appreciate the features and aspects of such embodiments, and others, upon review of the remainder of the specification.

BRIEF DESCRIPTION OF THE DRAWINGS

A full and enabling disclosure of the present invention, including the best mode thereof, directed to one of ordinary skill in the art, is set forth in the remainder of the specification, which makes reference to the appended Figures, in which:

FIG. 6 is an enlarged and isolated generally side perspective view of a present exemplary embodiment of a battery-operated device as otherwise represented in present FIG. 1 combination with other present components of an exemplary impotence treatment system according to the subject invention;

FIG. 7 is a longitudinal cross-sectional view of the exemplary embodiment of present FIG. 6, taken along the section line 7—7 as indicated therein;

Figure 1:
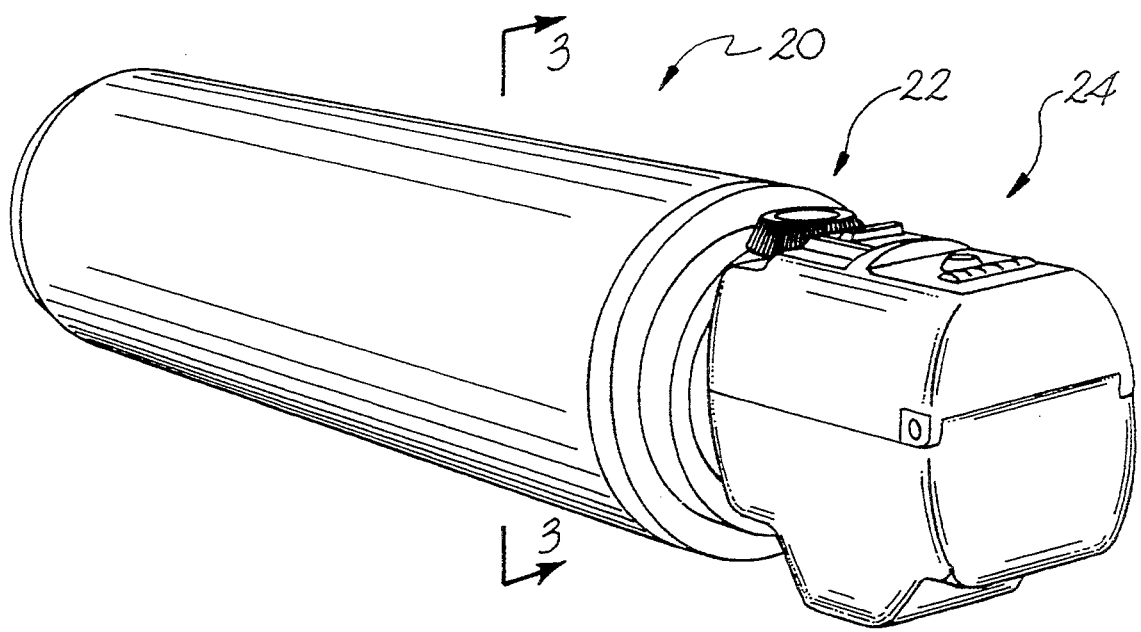
FIG. 1 is a generally side perspective view of an exemplary embodiment of the present invention, illustrating various separable components thereof in an inline assembled configuration for use with a battery-operated device.

Repeat use of reference characters throughout the present specification and appended drawings is intended to represent same or analogous features or elements of the invention.

DETAILED DESCRIPTION OF THE PREFERRED EMBODIMENTS

Figure 2:
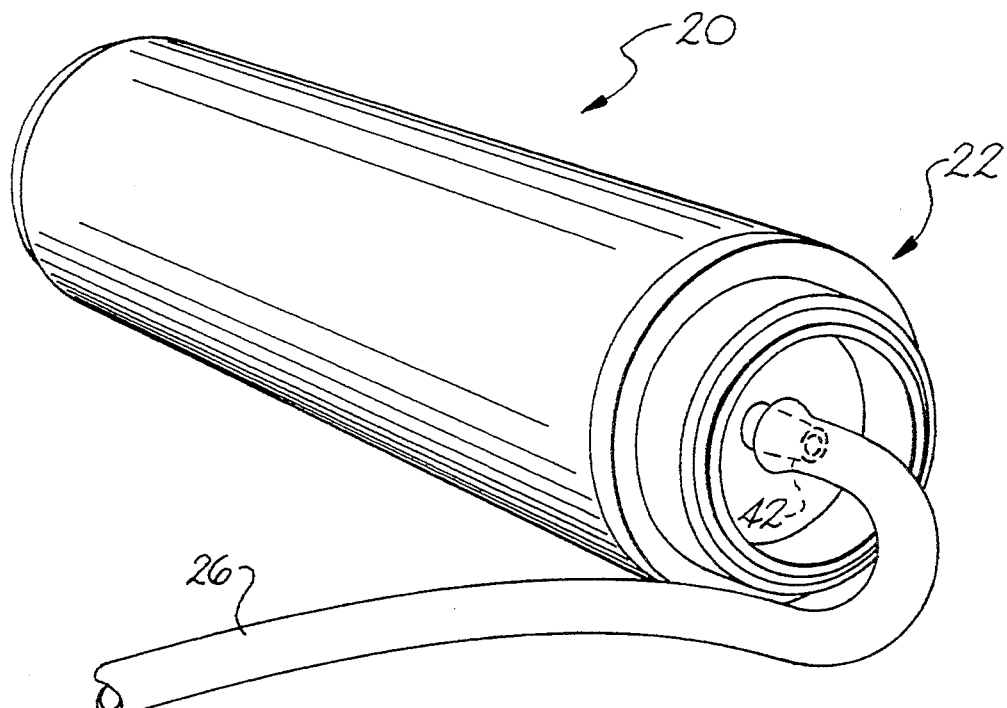
FIG. 2 is a generally side perspective view of the exemplary embodiment represented in FIG. 1, reconfigured for alternate use thereof with a vacuum tube interconnecting with an alternate vacuum source, such as a manual pump (not shown)

The present invention relates to various aspects of impotence treatment systems, including configurations of separable components as respectively illustrated in present FIGS. 1 and 2. Both such Figures show a generally side perspective view of an elongated vacuum chamber generally 20, such as may be comprised of optically transparent material, such as polycarbonate. As shown in FIG. 1, a reversible coupler and/or sealing element generally 22 is placed between the vacuum chamber 20 and a self-contained, battery-operated pump apparatus, generally 24. As will be discussed in greater detail below, coupling element 22 has a vacuum sealing face thereof adapted for receipt of an inline mounting of hand held unit 24. The sealing face is specifically arranged to mate with a vacuum connection port on device 24.

In accordance with another aspect of the subject invention, as represented by present FIG. 2, coupler 22 may assume a reversed position in an open end of chamber 20, so as to present a different axial side thereof for vacuum seal attachment of a vacuum tube 26. Such reversibility of coupler 22 permits use of chamber 20 with either a power assisted device, such as hand held unit 24, or an alternate vacuum source, such as a hand pump connected via tubing 26. For example, a device such as manual vacuum pump 46 of commonly assigned U.S. Pat. No. 4,856,498 (which patent is fully incorporated herein by reference), may be practiced with vacuum tubing 26. Other alternative vacuum sources may also be practiced in accordance with the subject invention.

Figure 3:
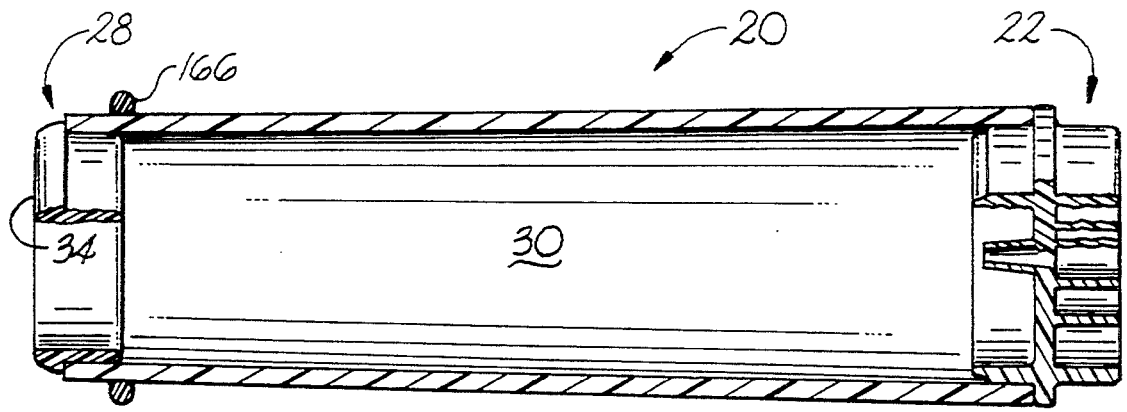
FIG. 3 is a longitudinal cross-sectional view of the vacuum chamber and reversible coupler components of the subject invention as represented in FIG. 1, taken along the section line 3—3 as indicated therein.

As indicated by new line 3—3 in FIG. 1, FIG. 3 illustrates a longitudinal cross section of vacuum chamber 20 and reversible coupler 22. FIG. 3 well illustrates certain preferred aspects of vacuum chamber 20. For example, a first open end generally 28 is provided for introduction of a user's penis into the chamber interior 30. An opposite open end generally 32 is provided for the introduction of negative pressure, as discussed below. An annular elastomeric seal element generally 34 may be removably received in the inside diameter of first end 28. Such element 34 (shown in partial cut away in FIG. 3) facilitates greater user comfort as vacuum chamber 20 is pressed against the user's body, and also helps establish and maintain a proper vacuum seal between the chamber and the user's body. Of course, an effective vacuum seal is essential to the overall vacuum engorgement therapy.

Furthermore, annular element 34 may be readily removed, just as reversible coupler 22 may be so removed, with a result that the vacuum chamber 20 is very easy to clean by being fully submersed. Again, given circumstances, cleanliness can be a very important issue.

Another aspect of the subject invention is represented well by present FIG. 3, in that vacuum chamber 20 may be preferably slightly tapered so that the inside diameter thereof reduces from end 32 towards end 28. The resulting increased opening towards the reversible coupler allows for the more full and complete expansion of the glans penis. Sometimes the enlargement of the glans penis (and other portions of the penis) is greater with vacuum therapy than otherwise occurs with an unaided totally natural erection, because the blood engorgement produced by the vacuum force is more complete than otherwise occurs in the unaided erection. The "inverse" taper arrangement of the cylinder accommodates such expansion. It is also not unusual for a slight degree of fullness to be lost during the process of applying the cincture band. Hence, some added fullness in the initially obtained engorgement level may help to achieve an ultimately larger or more full erection.

Still further, some users experience a degree of bending or angularity of the penis during erection. The inverse taper of the vacuum chamber 20 would accommodate such to a greater extent, without contact of the sensitive glans penis portion with the chamber interior.

Generally speaking, a taper angle of about 1 degree is preferred, though variations may be practiced. For example, the inside diameter of the first open end 28 may be in a range generally of from about 1.75 inches to about 2.25 inches, with an opening of 2.0 inches used in one preferred embodiment. On the other hand, the inside diameter of second open end 32 may be in a range of from about 2.0 inches to about 2.75 inches, with an inside diameter of 2.3 inches used in one preferred embodiment. The length of vacuum chamber 20 may also vary, such as in an exemplary arrangement of from about 7 inches to about 10 inches, with a length of 8.75 inches used in one preferred embodiment. A chamber wall thickness in a range of from about 0.1 inches to about 0.2 inches may be practiced (as well as others), with 0.185 inches used in one preferred embodiment.

Figure 4:
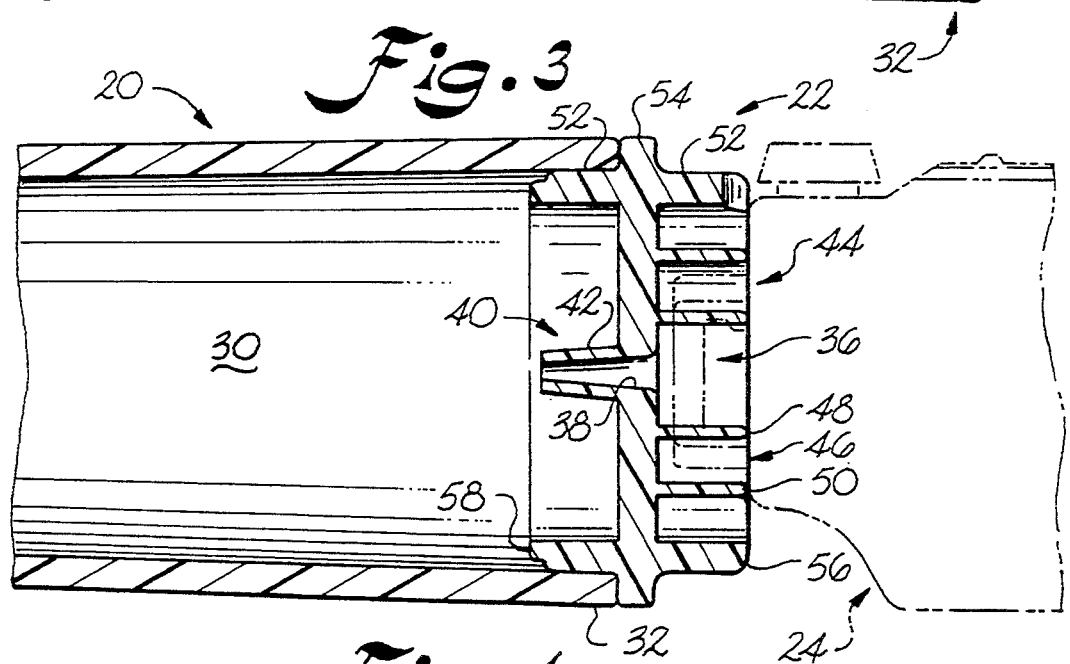
FIG. 4 is an enlarged, partial longitudinal cross-sectional view of the FIG. 3 and FIG. 1 embodiments, showing the exemplary configuration thereof with a battery-operated device.

While FIG. 3 illustrates reversible coupler 22 in partial cut away, FIG. 4 more fully indicates details thereof by a complete cross-sectional view. FIG. 4 also represents (in dotted line) a partial view of hand held device 24, and the vacuum seal relationship of a vacuum port generally 36 thereof, with a vacuum sealing face (one axial side) of reversible coupler 22.

Reversible coupler 22 also may be characterized as comprising a reversible coupling and vacuum seal means, removably receivable in the vacuum chamber second open end 32 so as to seal same against air flow except through a vacuum port generally 38 defined by element 22. A first vacuum port connection element generally 40 is provided on one axial side of element 22, for vacuum seal attachment of a vacuum tube (generally 26) to the vacuum port 38. In the illustrated exemplary embodiment, such first vacuum port connection element may comprise a vacuum tube connection nipple 42 extending from the location of the vacuum port 38. As shown, such vacuum port 38 preferably may comprise an axial bore generally along the central axis of the elastomeric seal element 22. Other locations may be practiced in alternative embodiments so long as a controlled sealing arrangement is maintained in accordance with the broader aspects of the subject invention.

A second vacuum port connection element generally 44 may be provided on a reverse or opposite axial side of reversible coupler 22. Such connection element 44 provides for alternate vacuum seal attachment of a battery-operated vacuum motor means, such as self-contained device 24, to the vacuum port 38. Preferably, such device 24 has a collar mounting means generally 46 or similar, with which second vacuum port connection element 44 may be matingly received in a vacuum seal arrangement.

As shown in the illustrated exemplary preferred embodiment, such second vacuum port connection element 44 may comprise a pair of concentric elements 48 and 50 projecting in an axial direction and concentric with the axial bore 38. As shown, one portion of the collar mounting means 46 is received in a generally interference fit on the inside diameter of inner concentric element 48, while another feature of the collar mounting means generally 46 is an annular element received in the annular space defined between the inner and outer concentric elements 48 and 50. Such collar mounting means features 46 are illustrated in dotted line in present FIG. 4, and are discussed in greater detail below.

A battery-operated vacuum motor means, such as device 24, provides a source of negative pressure at an intake port, generally 36, thereof. Such vacuum motor means further includes a collar mounting means generally 46 as represented, about the intake port generally 36 thereof, for selectively establishing a vacuum seal attachment between the intake port 36 and the second vacuum port connection element 44, as shown in present FIGS. 1 and 4. With the reversible coupling and vacuum seal means 22 received in the vacuum chamber second open end generally 32 in the illustrated configuration of FIGS. 1 and 4 of the present separable components, the sealing face 44 is essentially outwardly exposed. Whenever properly coupled, the negative pressure provided at port 36 is transmitted via the vacuum port 38 to the interior 30 of vacuum chamber generally 20. Thereafter, such negative pressure beneficially produces vacuum engorgement of a user's flaccid penis introduced thereto, as understood by those of ordinary skill in the art without additional discussion of physiological forces at work.

With further reference to the cross-sectional view of FIG. 4, the reversible coupling and vacuum seal means generally 22 preferably may comprise a generally circular elastomeric seal having a main outside diameter, generally 52. Such outside diameter slightly increasingly is tapered towards a radially outward flange generally 54 located between opposing axial projections 56 and 58 of such outside diameter 52. With such an arrangement, the elastomeric seal 22 may selectively be applied in a slightly interference fit in the vacuum chamber second open end generally 32, with the radially outward flange 54 seated against the end of vacuum chamber 30.

Figure 5:
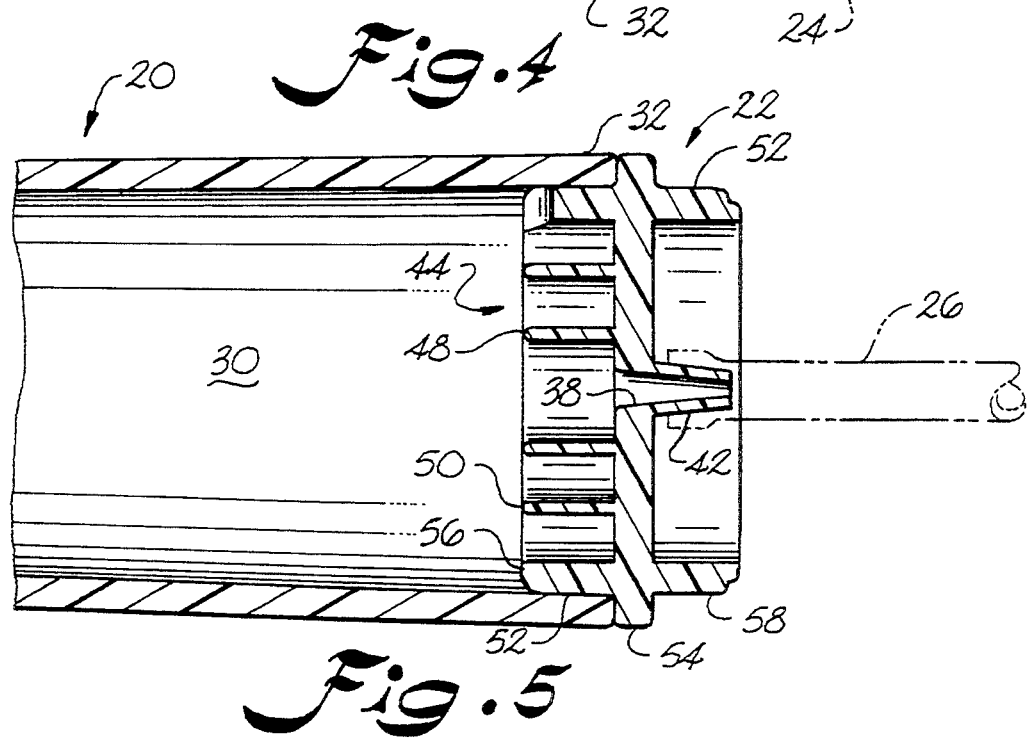
FIG. 5 is an enlarged, partial longitudinal cross-sectional view similar to the view of present FIG. 4, and illustrating the alternate vacuum source configuration of the subject invention as represented by present FIG. 2.

As is apparent from a comparison of present FIGS. 4 and 5, a selected one of the vacuum port connection elements 40 or 44 may be turned axially outward from the vacuum chamber 20 so as to be outwardly exposed for vacuum seal attachment thereto.

FIG. 5 comprises a further enlarged, cross-sectional partial view of vacuum chamber 20, with a reversible coupler 22 seated therein, in a condition reverse to that of the illustrated FIG. 4 configuration. With such arrangement, vacuum nipple 42 is outwardly turned for receipt of the end of a vacuum tube 26 thereon, as will be well understood by those of ordinary skill in the art from the specific illustration of present FIG. 5.

It is to be further understood that various elastomeric materials or the like, or equivalent substitutions therefor, may be practiced in accordance with the subject invention, either for reversible coupler 22, or for removable annular element 34. Also, different sizes and arrangements of the elastomeric seal 22 may be practiced. For example, the total axial length of element 22 (i.e., the length in the longitudinal axis direction of vacuum chamber 20) may generally be in a range of from about 1.0 inches to about 1.5 inches, with a length of 1.187 inches in one preferred embodiment.

As shown, the radially outward flange 54 is located in the approximate axial middle of such elastomeric seal 22, though off-center locations may be practiced in some embodiments. Also, the outside diameters of the pair of concentric elements 48 and 50 may fall in various ranges. For example, the outside diameter of the inner concentric element 48 may be generally in a range of from about 0.6 to about 0.75 inches, with 0.682 inches used in one preferred embodiment. The outside diameter of the outer concentric element 50 may be in a range of from about 1.3 inches to about 1.45 inches, with an outside diameter of 1.370 used in one preferred embodiment.

Figures 6, 7:
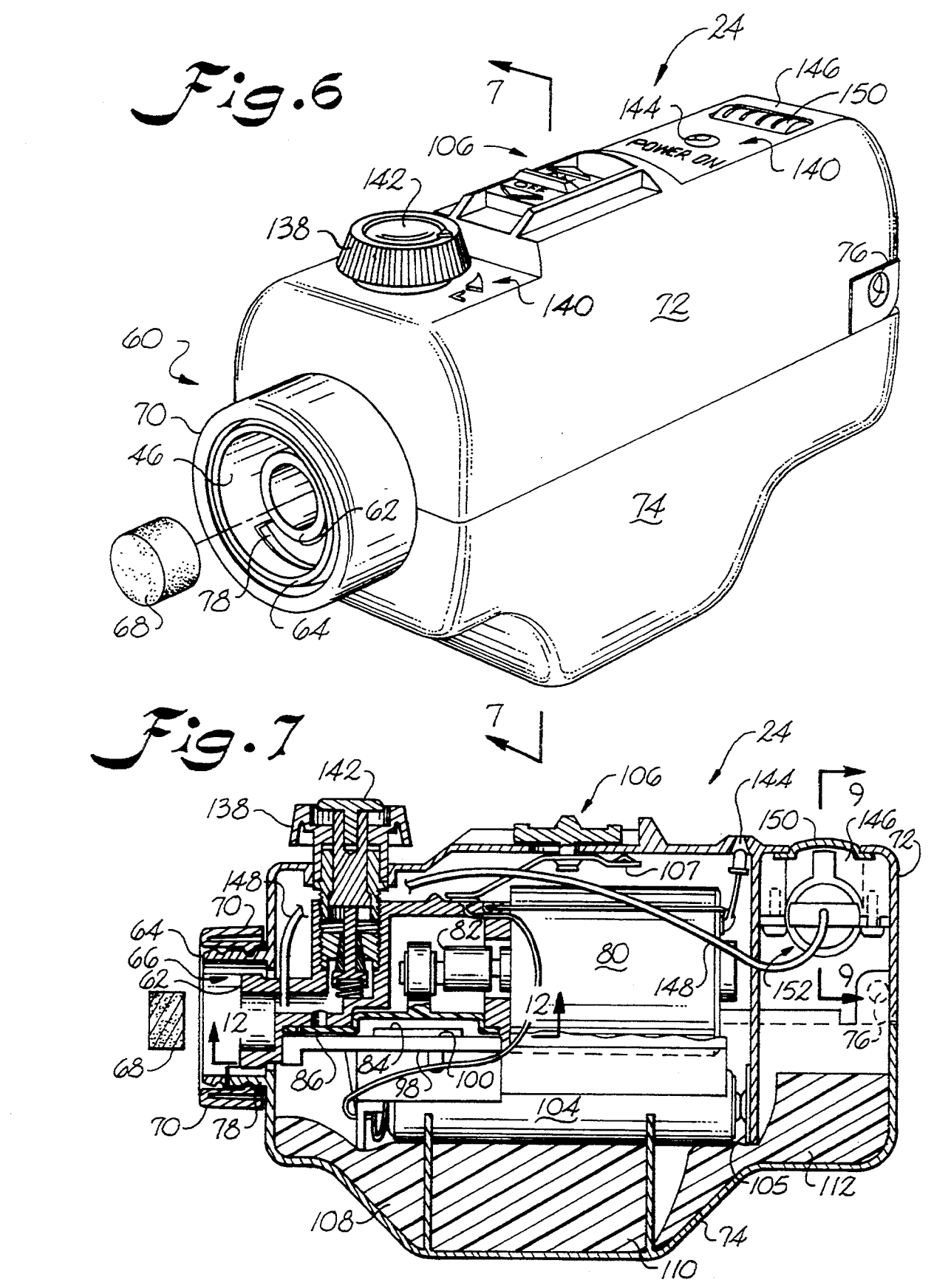

FIG. 6 illustrates a generally side, perspective view of the hand held device 24, as shown from an opposite side of the generally perspective view in present FIG. 1 as mounted therein on a vacuum chamber 20. Such hand held device 24 may comprise inline vacuum pump means in accordance with the subject invention. Generally speaking, such preferred embodiment of device 24 incorporates a battery-powered electric motor and airflow pump arrangement with a vacuum connection port generally 60.

Such port 60 provides for inline removable attachment to a predetermined axial side of the reversible coupler element 22, as represented in present FIGS. 1 and 4, and as discussed in detail above. With such an arrangement, the pump means 24 provides negative pressure to the interior 30 of vacuum chamber 20 whenever coupled thereto with reversible coupler 22 and via the vacuum connection port 60 and reversible coupler central bore 38. As understood by those of ordinary skill in the art, such an arrangement provides for the possibility of therapeutic engorgement of the user's flaccid penis received inside chamber 20.

The vacuum connection port or collar mounting means generally 60 may include a first generally circular intake element 62 projecting from the vacuum motor means and a second generally annular collar 64 projecting from the vacuum motor means and concentric with the first intake element 62 so as to form an annular space generally 66 therebetween. A particulate filter, such as a 50 micron filter of foam material, generally 68 may be provided in circular intake element 62 so as to reduce particulate matter inside device 24.

As represented by the view line 7—7 in FIG. 6, FIG. 7 comprises a generally longitudinal cross-sectional view of the embodiment of present FIG. 6. Such two Figures together illustrate that a further collar element 70 may be received (preferably in a snap fit) about element 64. Such collar 70 is a further factor in the effective seal arrangement shown by the mating reception of the sealing face generally 44 of reversible coupler 22 and the above-described features of hand held device 24, as specifically represented in the cross-sectional view of present FIG. 4.

FIGS. 6 and 7 further illustrate mutually closable first and second (i.e., upper and lower) housing elements or members 72 and 74, respectively. A mutually pivotable arrangement about pivot point 76 is preferred. With such arrangement, removable attachment of collar 70 renders element 64 and a separate portion 78 thereof (associated with lower housing number 74) as a collar mounting means. With application of collar 70, the two housing members 72 and 74 are actually held in their mutually closable state.

In other words, the elements 64 and 78 as illustrated in present FIGS. 6 and 7 represent respective joinable collar mounting elements associated with upper and lower housing elements 72 and 74, respectively, which cooperate whenever the housing members are brought together so as to form a circular mounting surface for removable receipt of collar mounting means annular collar 70 thereon. By the snap fit arrangement of such collar 70 onto the collected circular mounting surface defined by elements 64 and 78, the housing members are removably held together.

It is to be further understood by those of ordinary skill in the art, from the present discussion and from the illustrations of present FIGS. 1, 4, 6, and 7, that hand held device 24 comprises a self-contained hand held battery-operated vacuum motor apparatus for removable inline mounting onto the vacuum connection end of a penile receiving vacuum chamber. With such arrangement, the therapeutic treatment of impotence is provided with a power assisted device, in accordance with the subject invention.

It is to be further understood that the intake coupling port generally 46 defines a relatively airtight passage between the exterior and interior of the housing members 72 and 74 whenever mutually closed.

Figure 11:
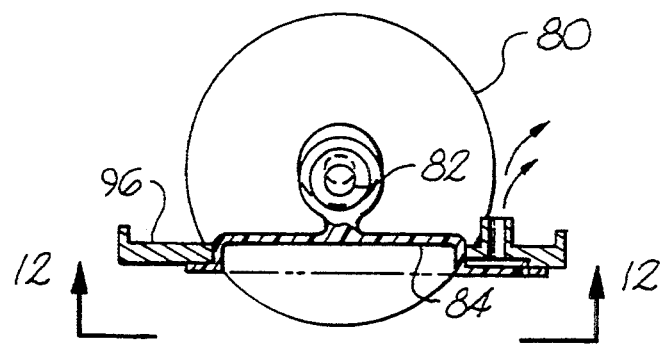
FIG. 11 is an isolated, partial cross-sectional view of certain present motor and pump features of the subject invention.

A battery-operated electric motor generally 80 may also be mounted inside the mutually closed housing members. As illustrated, such motor preferably may have an eccentric output shaft 82. FIG. 11 also illustrates a generally shaft end view of motor 80, thereby further demonstrating the eccentric nature of output shaft 82 thereof, and the relationship of such output shaft to pump features in accordance with this invention.

Figure 12:
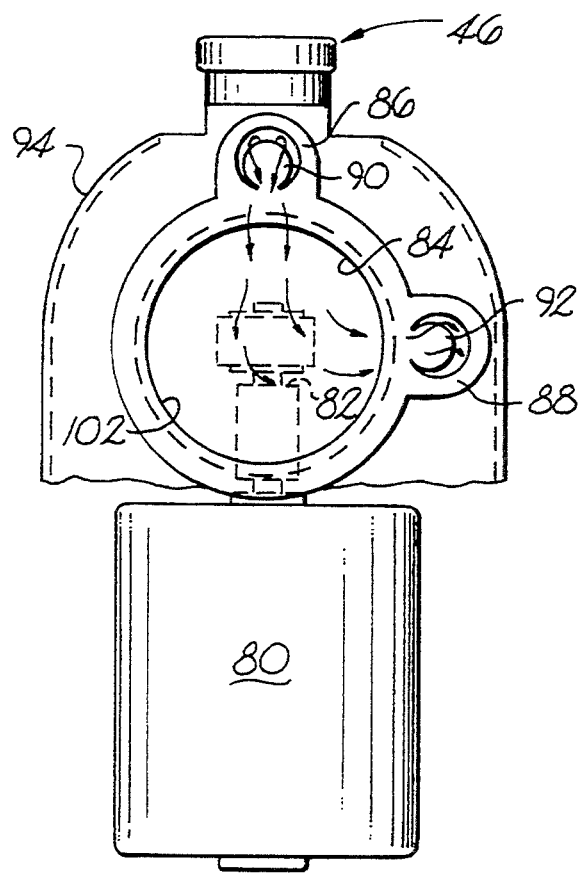
FIG. 12 is a generally bottom plan view of certain exemplary motor and pump features of the subject invention, generally as indicated by the view lines 12—12 in present FIGS. 7 and 11.

Those of ordinary skill in the art are familiar with reciprocating diaphragm pump means, as may be beneficially utilized in the subject invention. A diaphragm 84 (FIGS. 7, 11, and 12) is coupled with the eccentric output shaft 82 so as to be reciprocated (driven up and down) by operation of motor 80. An inlet air path generally 86 and an outlet air path generally 88 are accommodated with independently movable diaphragm elements 90 and 92, respectively, as understood by those of ordinary skill in the art. As represented in the Figures, such diaphragm 84 is captured between opposing sealed areas defined such as by various illustrated elements 94, 96, 98, and 100, so as to pump air along paths 86 and 88 and under circular area 102, as represented by the air flow arrows shown in present FIG. 12. FIG. 12 represents a generally bottom plan or elevational view of motor 80 and various present pump features, as represented by the view line 12—12 in present FIGS. 7 and 11.

Those of ordinary skill in the art will appreciate further features and aspects of the present pump means from the Figures presented herewith, without additional detailed disclosure thereof, which additional features form no particular aspect of the subject invention. In addition, those of ordinary skill in the art will recognize that various known substitutes may be practiced as to the pump features shown herein, or as substitute therefor. For example, pump arrangements as represented in Morifuji (U.S. Pat. No, 4,886,494) and Morifuki (U.S. Pat. No. 4,883,464), may be variously incorporated into and/or practiced in accordance with this invention or in substitution for pump or other features shown herein. The disclosure of such patents is fully incorporated herein by reference. Reference may also be had to Aida et al. (U.S. Pat. No. 4,759,747) and Schlensog et al. (U.S. Pat. No. 4,673,388), which also pertain to small scale pump arrangements, and the disclosures of which are fully incorporated herein by reference as examples of features which may be practiced in accordance with the subject invention.

As represented by present FIGS. 6 and 7, the housing members 72 and 74 cooperatively form a battery compartment such as for receipt of battery or batteries 104, which may be used for powering motor 80. In one embodiment, durable battery contact arrangements 105 have been provided with 0.008 inch thickness of beryllium copper. Standard A size, AA size, or AAA size batteries (or other) may be practiced, as called for by motor selection and other criteria, which may be undertaken by those of ordinary skill in the art when applying the subject invention to specific embodiment considerations.

For the present exemplary embodiment of the subject invention, one example of a suitable motor having a desired level of relatively higher torque and relatively lower energy consumption rates is the Mabuchi motor model RE-280SA-2865. Such motor has a 1.5 to 4.5 volt operating range, with a constant 3.0 volts nominal. At no load, the motor has an approximate speed of 7050 revolutions per minute, drawing a current of 0.160 amps. At maximum efficiency, the motor obtains a speed of 5950 revolutions per minute, drawing a current of 0.876 amps. Torque at such maximum efficiency point is 0.365 ounce-inches, with a 1.605 Watt output. Motor efficiency is 61 percent. A relatively high stall torque of 2.361 ounce-inches is obtained with such arrangement, so as to help avoid motor stall problems experienced with pumping operations.

With the foregoing illustrated embodiment and motor selection, test results have shown the achievement of a vacuum force of 10.4 inches mercury. With a flow rate of 1.2 liters per minute, a vacuum level of 5 inches of mercury has been achieved in an average of 5 to 7 seconds of operation, and with a vacuum level of 10 inches of mercury achieved in approximately 25 to 35 seconds.

The electric power switch means generally 106 is at least partially operatively associated with the exterior of the housing elements 72 and 74 so as to permit a user to control operation of motor 80 by batteries 104. The indicated arrangement provides an extremely low force level for operation, which further contributes to facilitating user convenience and adaptability to the use of the power-assisted embodiment 24. In one exemplary embodiment, durable but pliable switch contacts 107 have been provided with 0.012 inch thickness of beryllium copper.

FIG. 7 illustrates exemplary placement of various pre-cut foam elements 108, 110, and 112 which may be utilized interiorly to the mutually closable housing elements 72 and 74 for sound insulation. Such foam pieces may comprise virtually any form of usable foam, though lighter weight foams are preferred so as to maintain overall lightweight characteristics of the invention. The sound absorption achieved permits the use of a relatively more powerful motor, which furthers other present objects of the invention, as outlined above.

Various screw placements and the like for securing the motor mounting, and other features, will be well understood by those of ordinary skill in the art without additional disclosure, and may be variously practiced without detriment to the broader features of the subject invention. Hence, most screw placements are omitted for greater clarity in illustrating other aspects and features of the subject invention.

Figure 10:
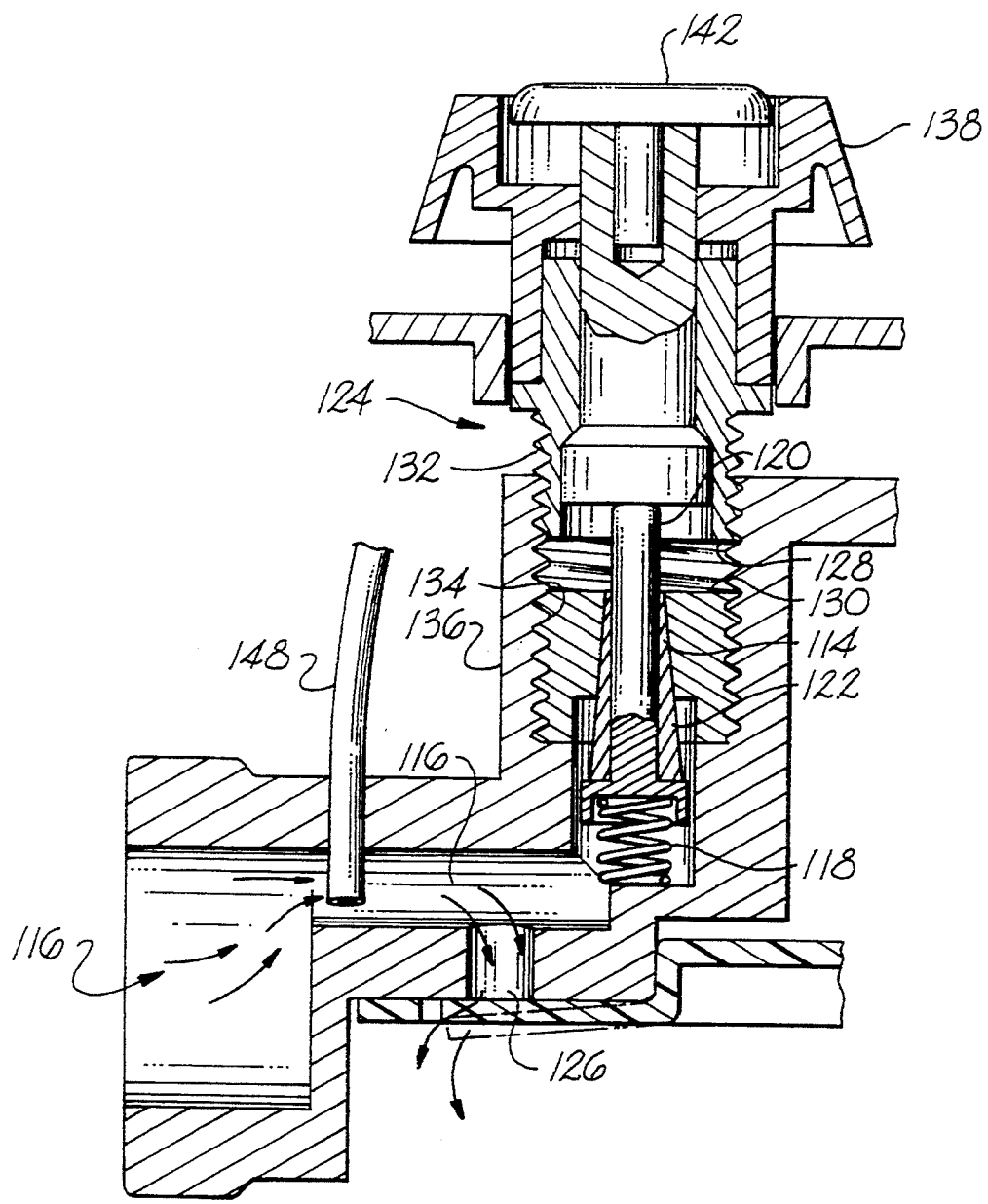
FIG. 10 is an enlarged, isolated cross-sectional view of a portion of the present features illustrated in the exemplary embodiment of present FIGS. 6 and 7, relating to flow control means, vacuum release means, and other present features.

FIGS. 6, 7, and 10 illustrate further features of the subject invention more specifically relating to user actuatable vacuum release means and user actuable flow control means. Both such means are operatively associated at least in part with the exterior of the mutually closed housing members 72 and 74, for user control or selection thereof. With the vacuum release means, a user may selectively vent the negative pressure produced in the intake coupling port with the pump means. Such venting action may be desired in the event of any discomfort for immediate relief thereof, or simply to help release the vacuum chamber from the body whenever it is time to be removed for intercourse.

The flow control means of the subject invention permits the user to select adjustment of the amount of negative pressure communicated to the intake coupling port, and hence to the interior of the vacuum chamber, in relation to the full negative pressure produced at the pump means air inlet.

FIG. 10 illustrates an enlarged view of a portion of the longitudinal cross section of present FIG. 7. As shown in both such Figures, a tapered bore 114 is provided for connecting the intake coupling port generally 116 with an alternative air pathway external to the mutually closed housing members 72 and 74. Such alternate air pathway is simply the non-airtight seals relative to the remaining elements in the upper half of FIG. 10. In other words, air escapes out (or comes in) through crevices in that portion of the housing. A biasing spring 118 is provided in conjunction with a piston 120 for mounting of tapered sealing element 122 movably within tapered bore 114. Such tapered sealing element 122 is selectively sized for receipt thereof in such tapered bore 114, as best illustrated in present FIG. 10.

Flow control means generally 124 in essence include partial actuation means for selectively placing and holding the piston 120 and the tapered sealing element 122 in a partially displaced position relative to tapered bore 114 so that a user selected portion of the negative pressure produced at the air inlet 126 is vented through the alternate air pathway described above. The distance between opposing surfaces 128 and 130 establishes an available adjusting gap for such maneuvering of tapered sealing element 122 relative to tapered bore 114.

As shown, the assembly 124 has threads 132 which engage threads 134 on the interior of housing portion 136. Such arrangement permits the entire assembly 124 to be rotated by grasping the upper actuation elements of FIG. 10 (such as knurled element 138, for rotating same). Thereby, fine adjustment of the vacuum force can be made by the user. With the top placement of such rotatable knob 138, user convenience is again provided. The capital letter "L" shown on the upper surface 140 in present FIG. 6 indicates the direction of rotation for slightly depressing element 122 so as to lower the effective vacuum force. A capital letter "H" may appear on the opposite side of upper surface 140, to indicate to the user the opposite adjustment to be made for increasing vacuum force to a higher level.

At the same time, a button 142 may be provided for rapid user depression of piston 120 to a complete state, so as to provide a user actuable vacuum release means, as indicated above. With such function, all of the negative pressure produced at the air inlet 126 is vented through the above-referenced alternate air pathway.

Also shown on the upper side 140 of upper housing member 72 is a "POWER ON" light indication. Such may comprise an external light means generally 144, such as an LED, for indicating the application of battery power to the motor. As shown particularly in present FIG. 7, such LED may be simply connected with the motor circuit so as to light whenever the motor is powered.

Figure 8:
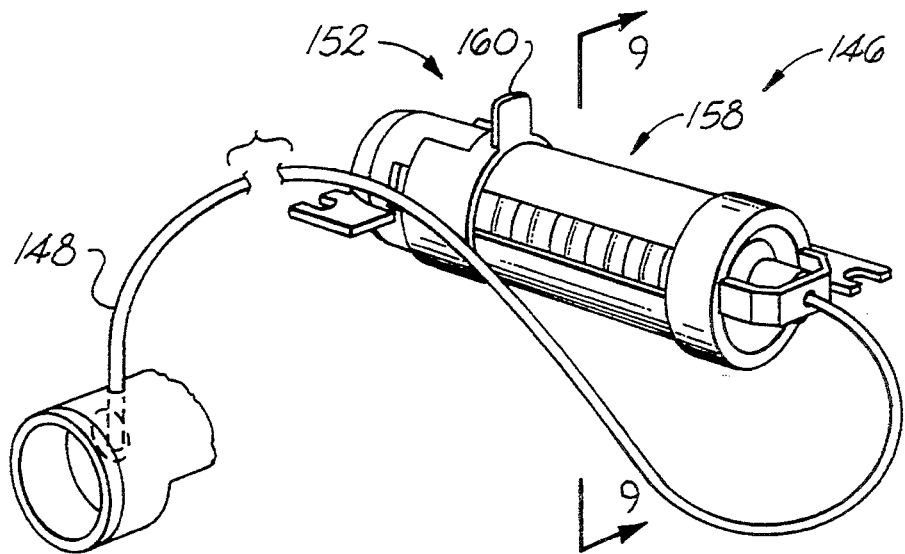
FIG. 8 is an enlarged and isolated perspective view of exemplary relative vacuum indicator means features in accordance with the subject invention, and as related to the exemplary embodiment of present FIGS. 1, 6, and 7.
Figure 9:
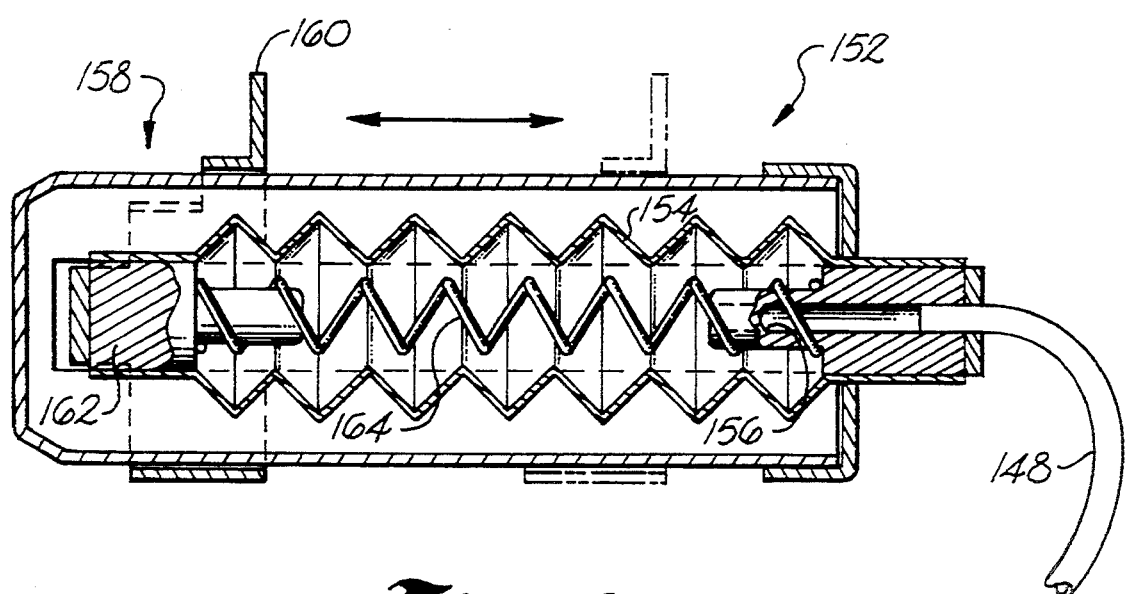
FIG. 9 is a further enlarged, generally longitudinal cross-sectional view of a portion of the relative vacuum indicator means features of present FIG. 8, taken along the section line 9—9 as indicated therein.

Still further shown on upper surface 140 for the user's convenience, is relative vacuum indicator means generally 146 in accordance with the subject invention. As shown by present FIGS. 6 and 7, such relative vacuum indicator means are again operatively associated at least in part with the exterior of the mutually closed housing members 72 and 74 so as to be convenient for the user. FIG. 8 illustrates an enlarged, isolated view of such relative vacuum indicator means generally 146, and FIG. 9 represents a longitudinal cross-sectional view of a portion of such Figures, as represented by sectional line 9—9 in present FIG. 8.

As represented by the airtight tubing generally 148 shown in present FIGS. 7—10, the relative vacuum indicator means 146 is also operatively associated with the intake coupling port generally 46 (FIGS. 6 and 12) and 116 (FIG. 10). Such fact permits the relative degree of negative pressure established in the intake coupling port to be indicated by means 146. With the particular features described hereinafter, a user may visually monitor and manually control the amount of negative pressure produced with the electric motor 80 and pump means of the subject invention, in a penile receiving vacuum chamber 20 removably associated with apparatus 24. The user is able to accomplish such beneficial function, even if the user is incapable of directly perceiving negative pressure on his penis with his physical senses. Thus, an object of the subject invention for improved comfort and safety during user controlled vacuum engorgement therapy treatments, is furthered by such features.

With reference particularly to present FIGS. 6 through 10, the following additional details are provided for an exemplary relative vacuum indicator means generally 146. A viewing window 150 may be formed in one of the housing members, such as upper element 72. A movable indicator device generally 152 may then be mounted inside the mutually closed housing members 72 and 74 beneath the viewing window 150 so as to be user viewable therethrough. The airtight tubing 148 interconnects the movable indicator device generally 152 with the intake coupling port, such as 116, as discussed above, so that the relative degree of negative pressure threat is communicated to the movable indicator device generally 152.

The movable indicator device 152 may generally comprise a bellows generally 154. Tubing 148 is connected to one end of bellows 154 through an opening 156 therein, as shown best in FIG. 9. With such arrangement, any negative pressure present in tube 148 is produced in the interior of bellows 154. Bellows 154 may be a rigid structure in some embodiments.

A guide sleeve generally 158 is received about bellows 154. A moving indicator element 160 is movably supported by the sleeve 158 external to bellows 154. At the same time, such moving indicator element 160 involves a bellows element 162, which is movably drawn in the bellows 154 towards tubing 148 in response to negative pressure produced in such tubing. As will be apparent to those of ordinary skill in the art, moving indicator element 160 moves in direct correspondence with any movements of bellows element 162.

A biasing spring 164 may also be received within bellows 154 between bellows element 162 and tubing 148. Such biasing spring 164 progressively opposes any movement of the bellows element 162 towards the tubing 148. As a result, any movement of the moving indicator element 160 (which is user visible through viewing window 150) results in indication of the relative degree of negative pressure in the tubing 148 and in the intake coupling port 46 or 116. In other words, element 162 is drawn towards tubing 148 to a progressively greater degree (overcoming the opposing bias of spring 164) in response to greater negative pressure forces in tubing 148.

Those of ordinary skill in the art will readily appreciate numerous variations which may be practiced in accordance with the subject invention, either by virtue of the expressed disclosure herewith, or the disclosure fully incorporated herein by reference. For example, in movable indicator device 152, spring 164 may be entirely omitted, in which case on equivalent biasing arrangement could be obtained by changing bellows 154 from a rigid structure to a resilient, collapsible structure. Bellows element 162 would then seal the end of bellows 154 opposite the one end thereof receiving the tube 148, such that bellows element 162 and its end of the bellows would move towards tube 148 as the bellows collapses due to the introduction of negative pressure thereto. The greater the negative pressure, the greater bellows 154 collapses, which is indicated by such embodiment of device 152.

For further example, the cross-sectional view of present FIG. 3 represents the presence and practice of an elastic cincture band 166 in accordance with the subject invention, received about the outside diameter of vacuum chamber 20 adjacent to end 28 thereof. As will be well understood by those of ordinary skill in the art, such cincture band may be applied to the root or base of a user's penis after adequate engorgement thereof. Elastic rings as represented by the above-referenced (commonly assigned and incorporated by reference) patents may be practiced. Still other alternatives may be practiced. For example, an elastic cincture band integrally including handles therewith for ease of manipulation may be practiced, such as shown by commonly assigned pending application U.S. Ser. No. 07/991,510 (now U.S. Pat. No. 5,244,4543 issued on Sep. 14, 1993). As also shown in such U.S. Pat. No. 5,244,453, an elastic cincture band may be further integrally provided with a urethra cradle for improved seminal discharge during climatic expulsion (i.e., ejaculation).

Still further, an elastic cincture band may further integrally include localized inside diameter pressure elements for predetermined alignment radially about the user's penis for improved cincturing thereof. See for example copending and commonly assigned design application U.S. Ser. No. 07/820,216 (now U.S. Pat. No. D343,455 issued Jan. 18, 1994) and utility patent application U.S. Ser. No. 07/883,083 (now U.S. Pat. No. 5,306,227 issued Apr. 26, 1994). Still further, an elastic cincture band may include an enlarged radially extending flange to prevent scrotal tissue intake with the band applied directly to the base of the user's penis during vacuuming operations. See for example the disclosure in copending and commonly assigned design application U.S. Ser. No. 07/830,061 (now U.S. Pat. No. D343,454 issued Jan. 18, 1994) and utility application U.S. Ser. No. 07/899,554 (now U.S. Pat. No. 5,234,402 issued Aug. 10, 1993).

The disclosures of all of the above-referenced commonly assigned U.S. Patents are fully incorporated herein by reference.

It should be further understood by those of ordinary skill in the art that the foregoing presently preferred embodiments are exemplary only, and the attendant description thereof is likewise by way of words of example rather than words of limitation, and their use does not preclude inclusion of such modifications, variations, and/or additions to the present invention as would be readily apparent to one of ordinary skill in the art, the scope of the present invention being set forth in the appended claims.

What is claimed is:

1. A self-contained, battery-operated male organ conditioning appliance, comprising:
    an elongated vacuum chamber, having a first open end adapted for introduction of a user's flaccid penis into said chamber, and a second open end for application of negative pressure to said chamber adequate so as to produce an erection in the user's flaccid penis, said chamber forming a reducing taper from said second open end thereof towards said first open end thereof;
    reversible coupling and vacuum seal means, with opposing sides thereof removably receivable in alternate directions in said vacuum chamber second open end so as to seal same against air flow except through a vacuum port defined thereby, said reversible coupling and vacuum seal means having on one side thereof a first vacuum port connection element for vacuum seal attachment of a vacuum tube to said vacuum port whenever said first vacuum port connection element is outwardly exposed, and a second vacuum port connection element on a reverse side thereof for alternate vacuum seal attachment of a battery-operated vacuum motor means to said vacuum port whenever said second vacuum port connection element is outwardly exposed; and
    battery-operated vacuum motor means for providing a source of negative pressure at an intake port thereof, said vacuum motor means further including a collar mounting means about said intake port thereof for selectively establishing a vacuum seal attachment between said intake port thereof and said second vacuum port connection element whenever said reversible coupling and vacuum seal means is received in said vacuum chamber second open end such that said second vacuum port connection element is outwardly exposed, so that negative pressure provided at said vacuum motor means intake port is transmitted via said vacuum port to the interior of said vacuum chamber for beneficially producing vacuum engorgement of a user's flaccid penis introduced thereto.

2. An appliance as in claim 1, wherein said vacuum chamber comprises transparent material, and has a first open end inside diameter in a range of from about 1.75 inches to about 2.25 inches, a second open end inside diameter in a range of from about 2.0 inches to about 2.75 inches, and a length in a range of from about 7 inches to about 10 inches, so that said vacuum chamber has a taper of generally about one degree.

3. An appliance as in claim 2, wherein said first open end inside diameter is about 2 inches, said second open end inside diameter is about 2.3 inches, and the length of said vacuum chamber is about 8.75 inches, with the wall thickness of said vacuum chamber being in a range from about 0.1 inches to about 0.2 inches.

4. An appliance as in claim 2, wherein:
    said transparent material comprises a polycarbonate; and
    said vacuum chamber further includes an annular seal removably received in said first open end thereof, adapted for promoting an effective vacuum seal between said chamber and a user's body whenever the user's penis is introduced into said chamber and said chamber is pressed against the user's body.

5. An appliance as in claim 2, wherein said reversible coupling and vacuum seal means comprises a generally circular elastomeric seal having a main outside diameter slightly increasingly tapered towards a radially outward flange located between opposing axial projections of said outside diameter, so that said elastomeric seal may selectively be applied in a slightly interference fit in said vacuum chamber second open end with said radially outward flange seated against said vacuum chamber and with a selected one of said vacuum port connection elements thereof turned axially outward from said vacuum chamber so as to be outwardly exposed for vacuum seal attachment thereto.

6. An appliance as in claim 5, wherein said elastomeric seal vacuum port comprises an axial bore generally along the central axis of said elastomeric seal, said first vacuum port connection element comprises a vacuum tube connection nipple extending from the location of said axial bore, and said second vacuum port connection element comprises a pair of concentric elements projecting in an axial direction and concentric with said axial bore for matingly receiving said collar mounting means of said vacuum motor means.

7. An appliance as in claim 6, wherein said elastomeric seal has a total axial length generally in a range of from about 1.0 inches to about 1.5 inches, with said radially outward flange located in the approximate axial middle of said elastomeric seal, and with said pair of concentric elements having outside diameters generally in the respective ranges of from about 0.6 inches to about 0.75 inches, and of from about 1.3 inches to about 1.45 inches.

8. An appliance as in claim 5, wherein said vacuum motor means further includes relative vacuum indicator means for indicating the relative negative pressure being transmitted from said intake port to the interior of said vacuum chamber.

9. An appliance as in claim 8, wherein:
said collar mounting means includes a first generally circular intake element projecting from said vacuum motor means and a second generally annular collar projecting from said vacuum motor means and concentric with said first intake element so as to form an annular space therebetween;
said elastomeric seal vacuum port comprises an axial bore generally along the central axis of said elastomeric seal; and
said second vacuum port connection element comprises a pair of inner and outer concentric elements projecting in an axial direction and concentric with said axial bore, said inner concentric element having an inside diameter sized for matingly receiving said collar mounting means first intake element and having a radial thickness sized for being matingly received in said collar mounting means annular space, and wherein said inner and outer concentric elements are annularly spaced so as to matingly receive said collar mounting means annular collar therebetween, so that said collar mounting means is removably attachable in a vacuum seal arrangement with said second vacuum port connection element.

10. An appliance as in claim 9, wherein said vacuum motor means includes first and second housing members pivotably attached to one another and having respective joinable collar mounting elements which cooperate whenever said housing members are brought together so as to form a circular mounting surface for removable receipt of said collar mounting means annular collar thereon, said annular collar having a snap fit on said circular mounting surface so as to hold said housing members together.

11. An appliance as in claim 10, wherein said vacuum motor means further includes received within said housing members thereof:
a battery-operated relatively high torque, low energy consumption electric motor with an eccentric output shaft;
reciprocating elastomeric diaphragm pump means associated with said eccentric output shaft so as to be driven thereby, for providing negative pressure to said intake port;
removable batteries for selectively operating said electric motor; and
sound absorbing foam for reducing electric motor noise external to said housing members.

12. An appliance as in claim 9, wherein said vacuum motor means further includes flow control means for user adjustment of the amount of negative pressure being produced at said intake port, and vacuum release means for user quick release of negative pressure established in said vacuum chamber with operation of said vacuum motor means.

13. Inline power assisted vacuum therapy impotence treatment apparatus with separable components to provide for alternate use thereof with a manually operated pump vacuum source, said apparatus comprising:
a vacuum chamber with opposing open ends, with one end adapted for introduction of a user's flaccid penis and with the other end for introduction of negative pressure to said chamber;
a generally round reversible coupler, having a generally central bore therethrough and having different first and second axial sides, for selectively sealing said chamber other end with a selected one of said axial sides of said coupler outwardly exposed, with said first axial side having an extending nipple for connecting an external vacuum tube in vacuum seal relationship with said central bore whenever said first axial side is outwardly exposed and with said second axial side having plural telescoped sealing elements for connecting an inline power assisted pump in vacuum seal relationship with said central bore whenever said second axial side is outwardly exposed; and
inline vacuum pump means, including a battery-powered electric motor and airflow pump arrangement with a vacuum connection port, for inline removable attachment to said reversible coupler second axial side whenever said second axial side is outwardly exposed and for providing negative pressure to said vacuum chamber when coupled thereto with said reversible coupler and via said vacuum connection port and said reversible coupler central bore, so as to provide therapeutic engorgement of a user's flaccid penis received in said chamber.

14. An apparatus as in claim 13, wherein said second axial side telescoped sealing elements comprise a pair of concentric annular elements centered about said central bore, and said vacuum pump means vacuum connection port comprises a generally round central member and an annular element concentric therewith, all sized for mating correspondence in a vacuum seal arrangement.

15. An appliance as in claim 13, wherein said vacuum chamber is slightly tapered towards said one end thereof so that the inside diameter of said other end thereof is generally larger than that of said one end.

16. An appliance as in claim 15, wherein said vacuum chamber comprises optically clear plastic and has a length of from about 7 inches to about 10 inches, with a taper of generally about one degree.

17. An appliance as in claim 16, wherein said vacuum chamber one end includes a removable elastomeric annular element adapted for cushioning and vacuum sealing said one end against the body of a user during use thereof.

18. An appliance as in claim 17, wherein said reversible coupler has a total axial length of from about 1.0 inches to about 1.5 inches, and has a radially outward flange located in the approximate axial middle thereof so as to be in sealing contact with said vacuum chamber regardless of which axial side of said reversible coupler is outwardly exposed.

19. An appliance as in claim 13, wherein said inline vacuum pump means further includes relative vacuum indicator means for indicating the relative negative pressure being provided to said vacuum chamber.

20. An appliance as in claim 19, wherein said inline vacuum pump means further includes a pair of mutually closable housing elements, flow control means for user adjustment of the amount of negative pressure being provided to said vacuum chamber, and vacuum release means for user controlled relatively quick venting of negative pressure in said vacuum chamber.

21. A multiple component impotence treatment system, comprising:
   a tapered enclosable vacuum chamber, with a reducing inside diameter towards a penis introducing end thereof and away from a vacuum introducing end thereof;
   an elastic cincture band, receivable about said vacuum chamber, adapted for transfer onto the base of a user's penis to capture and retain engorgement thereof produced by vacuum force while the user's penis is received in said vacuum chamber;
   a sealing coupling element removably received in the vacuum introducing end of said vacuum chamber, and having a central axis bore therethrough, which bore is surrounded on one axial side of said coupling element by a pair of concentric projections forming a vacuum sealing face; and
   an inline vacuum motor housing having annular vacuum port connection means for removable sealing attachments thereof to said sealing coupling element vacuum sealing face, a self-contained battery-operated electric motor, a vacuum pump operable by said motor and providing negative pressure to said annular vacuum port connection means, so that whenever said vacuum chamber, sealing coupling element, and inline vacuum motor housing components are properly assembled and said motor and pump operated, negative pressure is therapeutically administered to a user's flaccid penis so as to produce vacuum engorgement thereof suitable for intercourse, which engorgement is subsequently captured by said elastic cincture band so that the user's conditioned penis may be withdrawn from said vacuum chamber without loss of engorgement.

22. A system as in claim 21, wherein said sealing coupling element is reversible and has a coupling vacuum nipple on an axial side thereof opposite to said vacuum sealing face, so that said vacuum chamber and coupling element can be alternately used with an alternate vacuum source connected thereto at said nipple with a vacuum tube.

23. A system as in claim 21, wherein said elastic cincture band integrally includes handles therewith for ease of manipulation.

24. A system as in claim 23, wherein said elastic cincture band further integrally includes therewith a urethra cradle for improved seminal discharge during climatic expulsion.

25. A system as in claim 23, wherein said elastic cincture band further integrally includes localized inside diameter pressure elements adapted for predetermined alignment radially about the user's penis for improved cincturing thereof.

26. A system as in claim 23, wherein said elastic cincture band further includes an enlarged radially extending flange adapted to prevent scrotal tissue intake with said band applied directly to the base of the user's penis during vacuuming operations.

27. A system as in claim 21, further including:
   relative vacuum indicator means for indicating the relative negative pressure provided to said annular vacuum port connection means;
   flow control means for user adjustment of the amount of said negative pressure; and
   vacuum release means for user controlled venting of negative pressure provided in said vacuum chamber.

28. A self-contained hand held battery-operated vacuum motor apparatus adapted for removable inline mounting onto the vacuum connection end of a penile receiving vacuum chamber for the therapeutic treatment of impotence, said apparatus comprising:
   respective upper and lower mutually closable housing members;
   an intake coupling port defining a relatively airtight passage between the exterior and interior of said housing members whenever mutually closed;
   a battery-operated electric motor mounted in said mutually closed housing members, and having an eccentric output shaft;
   a battery compartment formed in said mutually closed housing members, adapted for removably receiving one or more batteries for driving said electric motor;
   motor power switch means, operatively associated with the exterior of said mutually closed housing members, for user selected control of operation of said motor whenever operating batteries are received in said battery compartment;
   reciprocating diaphragm pump means, having inlet and outlet air paths and associated with said eccentric output shaft so as to be driven thereby, for producing negative pressure at said air inlet thereof, said air inlet being in selectively airtight airflow communication with said intake coupling port;
   user actuatable vacuum release means, operatively associated with the exterior of said mutually closed housing members, adapted for user selected venting of negative pressure produced in said intake coupling port with said pump means;
   relative vacuum indicator means, operatively associated with the exterior of said mutually closed housing members and with said intake coupling port, for indicating to an apparatus user the relative degree of negative pressure established in said intake coupling port; and
   user actuatable flow control means, operatively associated with the exterior of said mutually closed housing members, adapted for user selected adjustment of the amount of negative pressure communicated to said intake coupling port in relation to the full negative pressure produced at said pump means air inlet, so that a user may visually monitor and manually control the amount of negative pressure produced with said electric motor and said pump means in a penile receiving vacuum chamber whenever such chamber is removably associated with said apparatus, even if the user is incapable of directly perceiving negative pressure on his penis with his physical senses, for improved comfort and safety during user controlled vacuum engorgement therapy treatments.

29. An apparatus as in claim 28, wherein said relative vacuum indicator means includes:

a viewing window formed in one of said housing members;

a movable indicator device mounted inside said mutually closed housing members beneath said viewing window so as to be user viewable therethrough; and airtight tubing interconnecting said movable indicator device with said intake coupling port so that the relative degree of negative pressure thereat is communicated to said movable indicator device.

30. An apparatus as in claim 29, wherein said movable indicator device comprises:

a rigid bellows with said tubing connected to one end thereof;

a guide sleeve received about said bellows;

a moving indicator element movably supported by said sleeve external to said bellows and having a bellows element which is movably drawn in said bellows towards said tubing in response to negative pressure in said tubing, said moving indicator element moving in direct correspondence with movements of said bellows element; and a biasing spring received in said bellows between said bellows element and said tubing, so as to progressively oppose movement of said bellows element towards said tubing, so that resulting movement of said moving indicator element visible through said viewing window indicates the relative degree of negative pressure in said tubing and in said intake coupling port, for application of such negative pressure to a penile receiving vacuum chamber.

31. An apparatus as in claim 29, wherein said movable indicator device comprises:

a resilient collapsible bellows with said tubing connected to one end thereof;

a guide sleeve received about said bellows and supporting same such that an opposite end of said bellows is relatively movable towards said one end thereof as said bellows collapses from the introduction of negative pressure thereto; and a moving indicator element movably supported by said sleeve external to said bellows and having a bellows element attached to said bellows opposite end for sealing same so as to move with said bellows opposite end as said bellows is progressively collapsed towards said one end thereof as negative pressure is applied via said tubing, said moving indicator element, moving in direct correspondence with movements of said bellows element so that resulting movement of said moving indicator element visible through said viewing window indicates the relative degree of negative pressure in said tubing and in said intake coupling port, for application of such negative pressure to a penile receiving chamber.

32. An apparatus as in claim 29, wherein:

said housing members are mutually pivotably mounted;

said intake coupling port further includes an axially projecting generally annular surrounding coupling collar mount collectively formed by respective elements of said mutually closed housing members, for aiding in the user selected establishment of a vacuum seal between said apparatus and the vacuum connection end of a penile receiving vacuum chamber; and wherein said apparatus further includes an annular coupling collar removably receivable on said coupling collar mount for holding together said mutually closed housing members.

33. An apparatus as in claim 32, wherein:

said flow control means includes a tapered bore connecting said intake coupling port with an alternate air pathway external to said mutually closed housing members, and a spring-biased, piston-mounted tapered sealing element selectively sized for receipt thereof in said tapered bore, said flow control means further including partial actuation means for selectively placing and holding said piston and said tapered sealing element in a partially displaced position relative to said tapered bore so that a user selected portion of said negative pressure produced at said air inlet is vented through said alternate air pathway; and wherein said vacuum release means comprises a user actuatable button for fully displacing said piston and said tapered sealing element relative to said tapered bore so that all of said negative pressure produced at said air inlet is vented through said alternate air pathway.

34. An apparatus as in claim 33, further including:

external light means for indicating the application of battery power to said motor;

a foam particulate screen received in said intake coupling port for reducing the entry of particles to said mutually closed housing members; and sound absorbing foam received in said mutually closed housing members for reducing the level of motor noise external to said housing members.

35. A reversible coupler adapted for use with a vacuum therapy impotence treatment system, such a treatment system as including a penile vacuum chamber, an elastic cincture band, a manual pump with interconnecting vacuum tubing, and an alternate battery-operated pump with an inline negative pressure port, said coupler comprising a generally circular elastomeric sealing member having a selectively sized main outside diameter slightly increasingly tapered towards a radially outward flange located between opposing axial projections of said outside diameter, such that said sealing member is adapted so as to be selectively applied in a slightly interference fit in one open end of a penile vacuum chamber with a selected one of first and second opposing axial sides of said sealing member outwardly exposed therefrom, said sealing member further including a vacuum port therethrough comprised of an axial bore generally along the central axis thereof, a first vacuum port connection element on said first axial side thereof adapted for selected vacuum seal attachment with interconnecting vacuum tubing of a manual pump, and a second vacuum port connection element on said second axial side thereof adapted for selected vacuum seal attachment with an inline negative pressure port of an alternate battery-operated pump.

36. A coupler as in claim 35, wherein said first vacuum port connection element comprises a vacuum tube connection nipple extending from the location of said axial bore.

37. A coupler as in claim 35, wherein said second vacuum port connection element comprises a pair of concentric elements projecting in an axial direction and concentric with said axial bore for matingly receiving the inline negative pressure port of an alternate battery-operated pump.

38. A coupler as in claim 37, wherein:

said first vacuum port connection element comprises a vacuum tube connection nipple extending from the location of said axial bore; and said elastomeric sealing member has a total axial length generally in a range of from about 1.0 inches to about 1.5 inches, with said radially outward flange located in the approximate axial middle of said elastomeric sealing member, and with said pair of concentric elements having outside diameters generally in the respective ranges of from about 0.6 inches to about 0.75 inches, and of from about 1.3 inches to about 1.45 inches.

* * * * *